United States Patent
Kwon et al.

(10) Patent No.: US 9,889,204 B2
(45) Date of Patent: Feb. 13, 2018

(54) POLYMERIC ANTIBIOTICS

(71) Applicant: The Regents of the University of California, Oakland, CA (US)

(72) Inventors: Young Jik Kwon, Irvine, CA (US); Julius Edson, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/823,930

(22) Filed: Aug. 11, 2015

(65) Prior Publication Data

US 2016/0038601 A1    Feb. 11, 2016

Related U.S. Application Data

(60) Provisional application No. 62/036,005, filed on Aug. 11, 2014.

(51) Int. Cl.

| | |
|---|---|
| *A61K 47/48* | (2006.01) |
| *A61K 31/7088* | (2006.01) |
| *A61K 31/722* | (2006.01) |
| *C08B 37/08* | (2006.01) |
| *A61K 47/61* | (2017.01) |

(52) U.S. Cl.
CPC ........ *A61K 47/4823* (2013.01); *A61K 31/722* (2013.01); *A61K 47/61* (2017.08); *C08B 37/003* (2013.01)

(58) Field of Classification Search
CPC . A61K 47/4823; A61K 31/00; A61K 31/7088
USPC .............................. 514/55; 536/20
See application file for complete search history.

(56) References Cited

U.S. PATENT DOCUMENTS

| | | | | |
|---|---|---|---|---|
| 5,057,542 A | * | 10/1991 | Leuba ..................... | A61K 8/736 424/401 |
| 5,510,418 A | * | 4/1996 | Rhee ..................... | C09J 189/06 525/54.2 |
| 6,503,897 B1 | * | 1/2003 | Beckett ................ | C07D 211/76 514/183 |

OTHER PUBLICATIONS

Patel et al, J. Pharm. Pharmaceut. Sci., 2010, 13(3), 536-557.*
Anisa, J.A. (Sep. 2002, e-published Jul. 13, 2002). "Stuart B. Levy: The antibiotic paradox. How the misuse of antibiotics destroys their curative powers, 2nd edn," *International Microbiology* 5(3):155-156.
Couvreur, P. et al. (Sep. 1991). "Liposomes and nanoparticles in the treatment of intracellular bacterial infections," *Pharm Res* 8(9):1079-1086.
Edson, J.A. et al. (Sep. 10, 2014, e-published Jul. 2, 2014). "RNAi for silencing drug resistance in microbes toward development of nanoantibiotics," *J Control Release* 189:150-157.
English, B.K. et al. (2010). "The Use and Abuse of Antibiotics and the Development of Antibiotic Resistance," *Advances in Experimental and Medicine and Biology* 659:73-82.
Fauci, A.S. et al. (May 14, 2014). "The perpetual challenge of antimicrobial resistance," *JAMA* 311(18):1853-1854.
Hale, C.R. et al. (Nov. 25, 2009). "RNA-guided RNA cleavage by a CRISPR RNA-Cas protein complex," *Cell* 139(5):945-956.
Huh, A.J. et al. (Dec. 10, 2011). "Nanoantibiotics": a new paradigm for treating infectious diseases using nanomaterials in the antibiotics resistant era, *J Control Release* 156(2):128-145.
Mourya, V.K. et al. (2008). "Chitosan-Modifications and Applications: Opportunities Galore," *Reactive & Functional Polymers* 68:1013-1051.
Gref et al, Science, 263:1600-1603 (1994).
Hwang et al, J. Control Release, 128:23-31 (2008).
Jiang et al, Mol. Pharm., 3:152-160 (2006).
Kim et al, Biomacromolecules, 6:1154-1158 (2005).
Kim et al, J. Control Release, 111:228-234 (2006).
Kim et al, J. Control Release, 127:41-49 (2008).
Lee et al, Colloid Polym Sci., 278:1216-1219 (2000).
Min et al, J. Control Release, 127:208-218 (2008).
Moghimi et al, Pharmacol. Rev., 53:283-318 (2001).
Ngawhirunpat et al, Colloids and Surfaces B: Biointerfaces, 74:253-259 (2009).
Seymour et al, Br. J. Cancer, 63:859-866 (1991).
Ye et al, Int. J. Pharm., 352:294-301 (2008).
Zhang et al, Nanomedicine, 3:258-265 (2007).

\* cited by examiner

*Primary Examiner* — Ganapathy Krishnan
(74) *Attorney, Agent, or Firm* — Mintz Levin Cohn Ferris Glovsky and Popeo, P.C.

(57) ABSTRACT

The disclosure provides, inter alia, polymeric antibiotic compounds such as modified chitosans and methods of use thereof.

21 Claims, 7 Drawing Sheets

FIG. 3
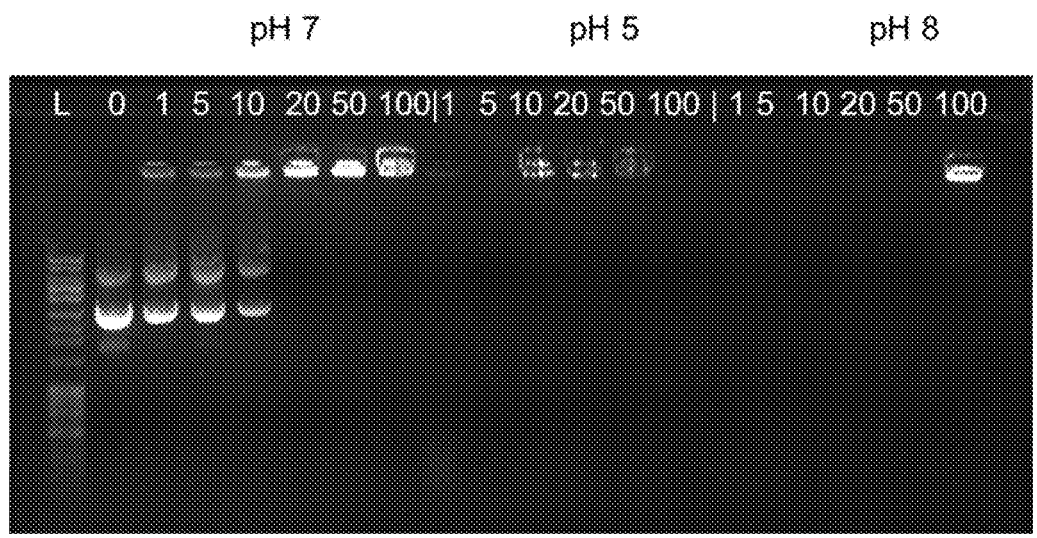
kChitosan Polyplex
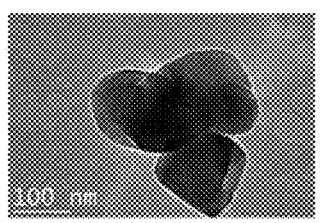
Native
FIG. 4A
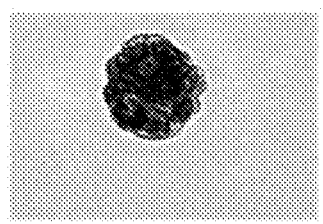
kChitosan
FIG. 4B
Hydrolyzed
FIG. 4C

POLYMERIC ANTIBIOTICS

CROSS-REFERENCES TO RELATED APPLICATIONS

This applications claims the benefit of U.S. Provisional Application No. 62/036,005, filed Aug. 11, 2014, the content of which is incorporated herein in its entirety and for all purposes.

STATEMENT AS TO RIGHTS TO INVENTIONS MADE UNDER FEDERALLY SPONSORED RESEARCH AND DEVELOPMENT

This invention was made with government support under grant number DGE-1321846 awarded by the National Science Foundation. The Government has certain rights in the invention.

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

This application relates, inter alia, to the field of polymer chemistry, and more particularly to reversible modification of natural polysaccharides.

One of the major challenges in the field of medicine is the rampant increase in cases of antimicrobial drug resistance. Small molecules based antimicrobials have the formation of drug resistance, which can be attributed to misuse of available antimicrobial. Almost all currently available conventional antibiotics have a microbe that has developed a resistance to that drug molecule through some mechanism of drug resistance formation.

Gene silencing has been recently shown to be possible in eukaryotic cells through the use of RNAi (micro (miRNA), double stranded (dsRNA), small interfering (siRNA), piwi (piRNA). With the recent advent of CRISPR RNA (crRNA), prokaryotic gene silencing becomes a possibility for treatment of drug resistant infections.

Antimicrobial materials have been present in the field of medicine for many years, with the most well-known being silver. Silver, as well as many other metals and metal oxides, such as gold, aluminum, zinc oxide, and titanium dioxide hinder or eliminate microbe growth either through reactive oxygen species (ROS) or physically hindering key biological processes. Furthermore there are a plethora of synthetic polymers and other nanoantibiotic material all of which destroy microbes through generation of ROS, cell membrane permeation, triggering DNA damage, or interrupting trans-membrane electron transport. The term nanoantibiotic refers to nanomaterials having antibiotic capabilities.

An added advantage of nanoantibiotics is the possibility to target intracellular infections which are usually the most difficult to target due to intracellular diffusion kinetics and lack of drug accessibility to desired locations. While a majority of these nanoantibiotic materials are very effective against microbes, some are toxic to the host cells as well and limits use. Moreover, with the focus of engineering new antimicrobial that encompasses gene silencing, a vector capable material is desired.

Chitosan is an abundant natural material that is biogradeable with no reported toxicity. Difficulties with chitosan lies in the lack of solubility in biologically relevant pH, and ineffective release. There is a need in the art for compositions and method to overcome this difficulties by improving solubility of chitosan, aiding in transfection of chitosan, and creating a process that can be applied to other polymeric nanoantibiotics. Provided herein are solutions to these and other problems in the art.

BRIEF SUMMARY OF THE INVENTION

The disclosure provides polymeric compounds of Formula (I):

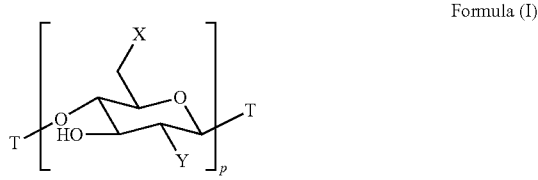

Formula (I)

wherein each Y is independently $-NH_2$, $-NH-C(=O)CH_3$, or a protecting group; each X is independently $-OH$, $-O-C(R^1R^2)-O-(CH_2-CH_2-O)_x-(CH_2)_y-R^3$, or $-O-C(R^1R^2)-O-D$; provided that at least one X is not $-OH$; p is 2 or more; x and y are each independently an integer from 1 to 10; each T is independently a terminal moiety; $R^1$ and $R^2$ are each independently H, a substituted $C_{1-6}$ alkyl group, an unsubstituted $C_{1-6}$ alkyl group, a substituted $C_{5-6}$ heteroalkyl group, or an unsubstituted $C_{5-6}$ heteroalkyl group; $R^3$ is $-NH_2$, $-C(=O)-R^4$, or $-NH_2-C(=O)-R^4$; and $R_4$ is D, a $C_{1-6}$ alkyl group, or a $C_{1-6}$ alkyl group substituted with one or more halogen atoms; and D is a drug moiety.

The disclosure provides polymeric compounds of Formula (II):

Formula (II)

wherein A is chitosan; L is a cleavable linking group; B is a drug moiety, a hydrophilic group, or a hydrophilic group linked to a drug moiety; and p is an integer greater than 2.

The disclosure provides compounds (e.g. ketal-chitosans) comprising the monomer of Formula (III):

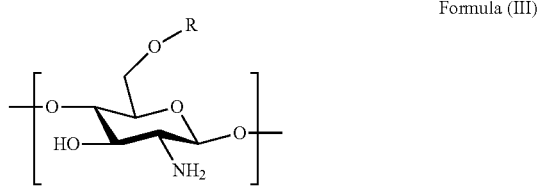

Formula (III)

wherein R is a optionally substituted heteroalkyl moiety forming a ketal with the chitosan monomer.

In another aspect, there is provided a pharmaceutical composition comprising the compounds described herein and a pharmaceutically acceptable excipient. In another aspect, there is provided a pharmaceutical composition comprising the compounds described herein, an antibiotic, and a pharmaceutically acceptable excipient In another aspect, there is provided a method of treating a bacterial infection in a subject in need thereof by administering a therapeutically effective amount of the compounds described herein (e.g., Formula (I), Formula (II)) to the subject to treat the bacterial infection. In another aspect, there is provided a method of treating a bacterial infection in a subject in need thereof by administering a therapeutically effective amount of the compounds described herein (e.g., Formula (I), Formula (II)) and an antibiotic to the subject to treat the bacterial infection. The compounds described herein and the antibiotic can be administered separately (e.g., in separate formulations at the preferred dosing schedule for each compound) or in the form of a single pharmaceutical composition.

In another aspect there is provided a method for synthesis of the compounds of Formula (I) and Formula (II), and ketal chitosans which includes protecting a chitosan monomer, reacting the protected chitosan with a half acetal moiety under conditions suitable to form a protected ketal chitosan, and deprotecting the protected ketal chitosan in order to afford a ketal chitosan (including the compounds of Formula (I) and (II)) described herein.

BRIEF DESCRIPTION OF THE FIGURES

FIG. 1A: DNA Size; FIG. 1B: siRNA size. FIG. 1C: DNA PDI; FIG. 1D: siRNA PDI; FIG. 1E: DNA Zeta; FIG. 1F: siRNA Zeta.

FIG. 2A: Size and PDI of exemplary compounds and hydrolyzed DNA. FIG. 2B: Size and PDI of exemplary compounds and hydrolyzed siRNA.

FIG. 3. Gel electrophoresis of compounds disclosed herein as a function of pH.

FIGS. 4A-4C. Transmission electron micrographs of indicated kChitosan polyplex compounds. FIG. 4A: Native; FIG. 4B: kChitosan; FIG. 4C: Hydrolyzed.

FIG. 7A: kChitosan/DNA polyplexes. Each group corresponds to concentration of 2.5, 5, 10, 20, 40 and 80 µM, left to right. Within each group, components are binned (left to right): naked DNA, NP 1, NP 3, NP 10, NP 20, NP 50, NP 100 and raw kChit. Groups at 2.5, 5 and 10 µM do not display entries for raw kChit. FIG. 7B: kChitosan/siRNA polyplexes. Each group corresponds to concentrations to 10, 20, 40 and 80 µM, left to right. Within each group, components are binned (left to right): PBS, naked siRNA, NP 10, NP 20, NP 50, NP 100 and NP 200. The term "NP" means "N/P ratio."

DETAILED DESCRIPTION OF THE INVENTION

Figure 1A:
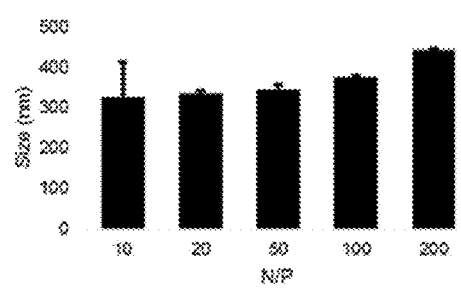
FIGS. 1A-1F.
Figure 1B:
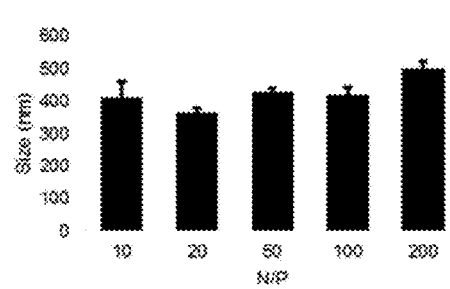
Figure 1C:
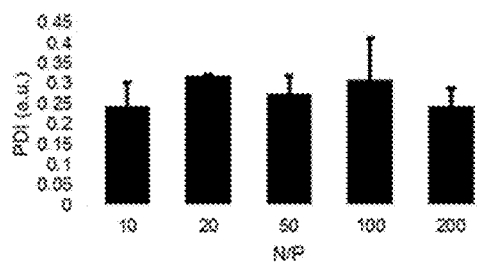
Figure 1D:
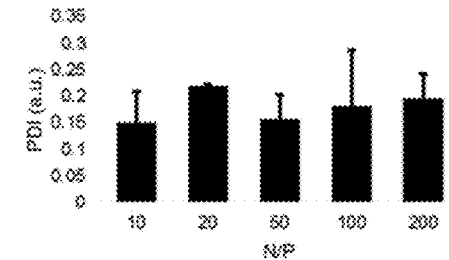
Figure 1E:
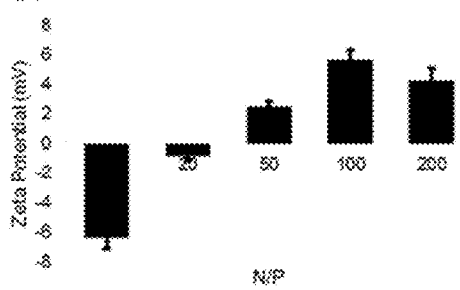
Figure 1F:
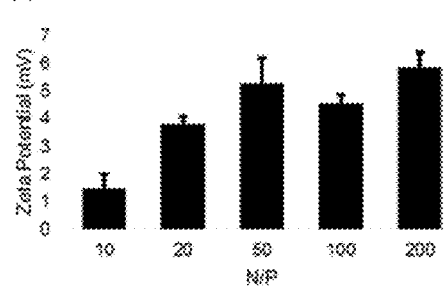

Chitosan is a molecule that under normal circumstances is not water soluble, and needs to be protonated in an acid environment to be active. Provided herein, for example, are ketal-chitosan (kchit) material disclosed herein in a neutral environment is water soluble to a certain concentration, at higher concentrations it becomes a suspension, and at acidic pH, kchit hydrolyzes returning to native chitosan. These transformations provide the material with unique features as a genetic vector for cancer therapy, matrix for tissue engineering, membrane for water treatment applications, and as an antibiotic. For example, in a nanoparticle carrying nuclei acids, once endocytozed the material will transition from kChit to Chitosan, during this change the nuclei acid is released but additionally native chitosan will be generated.

The advantages of the compounds disclosed herein (e.g., kChitosan, Formula (I), Formula (II)) include the following. First, temporary but stable modification maintain the material in its natural state since, e.g., the long time effects of extensive material modification are unknown. The reversibility of kChitosan provides additional advantage in fields where the antimicrobial characteristics are desired. Furthermore, the ketal linkage is stable long enough for solubility benefits while short enough that it would not hinder natural properties. Second, the compounds are organic and natural. Unlike other formulations the active primary amine of the sugar backbone of chitosan is left unmodified, thus leaving the material in its natural state, e.g., which results in less side effects.

The abbreviations used herein have their conventional meaning within the chemical and biological arts. The chemical structures and formulae set forth herein are constructed according to the standard rules of chemical valency known in the chemical arts. Where substituent groups are specified by their conventional chemical formulae, written from left to right, they equally encompass the chemically identical substituents that would result from writing the structure from right to left, e.g., —CH$_2$O— is equivalent to —OCH$_2$—.

"Chitosan" refers to a linear polysaccharide composed of randomly distributed monomers of β-(1,4)-D-glucosamine (a deacetylated monomer) and N-acetyl-D-glucosamine (acetylated monomer). In this disclosure, "chitosan" may be represented by the following Formula (IV):

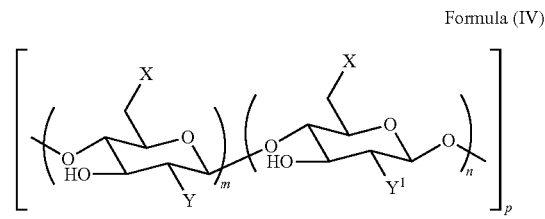

Formula (IV)

wherein X is a hydroxyl group; Y is an amine (i.e., thereby forming the β-(1,4)-D-glucosamine); Y$^1$ is —NH—C(=O)—CH$_3$ (i.e., thereby forming the N-acetyl-D-glucosamine); m, n, and p are integers of size to form the chitosan; and m and n are randomly distributed.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4- pentadienyl, 3-(1,4-pentadienyl), ethynyl, 1- and 3-propynyl, 3-butyryl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "heteroalkyl," by itself or in combination with another term, means, unless otherwise stated, a stable straight or branched non-cyclic chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NRNR"R'", —ONR'R", —NR'C=(O)NR"NR'"R"", —CN, —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:
  (i) oxo, halogen, —CF$_3$, —CN, —OH, —NH$_2$, —COOH, —CONH$_2$, —NO$_2$, —SH—SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, heteroaryl, substituted with at least one substituent selected from:
    (a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another. It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

The symbol " ⌇ " denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "protecting group" is used herein according to its plaining ordinary meaning as commonly used in the art. A protecting group is typically chemical moiety covalently bound to a functional group (e.g. a chemically reactive group) to prevent undesired chemical reactions, wherein the protecting group may be optionally removed (deprotected) thereby revealing the underlying functional group.

A "drug moiety" as used herein is a monovalent drug covalently attached to the remainder of the compound disclosed herein. The term "drug" is used herein in according to its plain ordinary meaning as used in the art. A drug is a compound that is biologically active and may be used as a treatment of a disease. Drugs may be, for example, a small molecule, a peptide, nucleic acid or a protein. Exemplary drugs include antibiotics, chemotherapeutic agents, and tuberculosis drugs. A drug moiety may include a linking moiety (e.g. $L^{1D}$) that covalently links the drug moiety to the remainder of the compound disclosed herein. The linking moiety may be a bond, —O—, —S—, —C(O)—, —C(O)NH$_2$—, —NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent.

Exemplary antibiotics include lipopeptides (e.g., daptomycin); macrocyclics (e.g., fidaxomicin); penicillins (e.g., amoxicillin, ampicillin, bacampicillin, carbenicillin, cloxacillin, dicloxacillin, flucloxacillin, mezlocillin, nafcillin, oxacillin, penicillin G, pencillin V, piperacillin, pivampicillin, pivmecillinam, ticarcillin); cephalosporins (e.g., ceftaroline, cefacetrile, cefadroxil, cephalexin, cefaloglycin, cefalonium, cefaloridine, cefalotin, cefapirin, cefatrizine, cefazaflur, cefazedone, cefazolin, cefradine, cefroxadine, ceftezole, cefaclor, cefamandole, cefmetazole, cefonicid, cefotetan, cefoxitin, cefprozil, cefuroxime, cefuzonam, cefcapene, cefdaloxime, cefdinir, cefditoren, cefetamet, cefixime, cefmenoxime, cefodizime, cefotaxime, cefpimizole, cefpodoxime, cefteram, ceftibuten, ceftiofur, ceftiolene, ceftizoxime, ceftriaxone, cefoperazone, ceftazidime, cefclidine, cefepime, cefluprenam, cefoselis, cefozopran, cefpirome, cefquinone, ceftobiprole, ceftaroline, cefaclomezine, cefaloram, cefaparole, cefcanel, cefedrolor, cefempidone, cefetrizole, cefivitril, cefmatilen, cefmepidium, cefovecin, cefoxazole, cefotil, cefsumide, cefuracetime, ceftioxide); monobactams (e.g., aztreonam); carbapenems (e.g., imipenam, imipenam, cilastatin, doripenem, meropenem, ertapenem); macrolides (e.g., azithromycin, erythromycin, clarithromycin, dirithromycin, roxithromycin); ketolides (e.g., telithromycin); lincosamides (e.g., clindamycin, lincomycin); streptogramins (e.g., pristinamycin, quinupristin, dalfopristin); aminoglycosides (e.g., amikacin, gentamicin, kanamycin, neomycin, netilmicin, paromomycin, streptomycin, tobramycin); quinolones (e.g., flumequine, nalidixic acid, oxolinic acid, piromidic acid, pipemidic acid, rosoxacin, ciprofloxacin, enoxacin, lomefloxacin, nadifloxacin, norfloxacin, ofloxacin, levofloxacin, pefloxacin, rufloxacin, balofloxacin, gatifloxacin, grepafloxacin, moxifloxacin, pazufloxacin, sparfloxacin, temafloxacin, tosufloxacin, besifloxacin, clinafloxacin, gemifloxacin, sitafloxacin, trovafloxacin, prulifloxacin); sulfonamides (e.g., sulfamethizole, sulfamethoxazole, sulfisoxazole); tetraclycines (e.g., demeclocycline, doxycycline, minocycline, oxytetracycline, oxytetracycline, tetracycline, tigecycline); chloramphenicol; metronidazole; tinidazole; nitrofurantoin; vancomycin; teicoplanin; lipoglycopeptides (e.g., telavancin); oxazolidinones (e.g., linezolid, cycloserine); rifamycins (e.g., rifampin, rifabutin, rifapentine); polypeptides (e.g., bacitracin, polymyxin B); tuberactinomycins (e.g., viomycin, capreomycin); and the like. In certain embodiments, the antibiotic drug is preferably a hydrophilic antibiotic drug.

"Tuberculosis" is an infectious disease that typically attacks the lungs, but is capable of attacking most parts of the body. Tuberculosis is caused by *Mycobacterium tuberculosis*, and is spread from person to person through the air. In embodiments, the drug (D) is a tuberculosis drug. Exemplary tuberculosis drugs include isoniazid, rifampicin, pyrazinamide, ethambutol, streptomycin, and the like. In certain embodiments, the tuberculosis drug is preferably a hydrophilic tuberculosis drug.

"Chemotherapeutic agent" is refers to a compound having antineoplastic properties or the ability to inhibit the growth or proliferation of cells. Exemplary chemotherapeutic agents include alkylating agents (e.g., nitrogen mustards, nitrosoureas, alkyl sulfonates, triazines, ethylenimines); antimetabolites (e.g., 5-FU, 6-MP, capecitabine, cytarabine, floxuridine, fludarabine, gemcitabine, hydroxyurea, methotrexate, pemetrexed); anthracylines (e.g., daunorubicin, doxorubicin, epirubicin, idarubicin); actinomycin-D, bleomycin, mitomycin-C; topoisomerase inhibitors (e.g., topotecan, irinotecan, etoposide, teniposide, miloxantrone); mitotic inhibitors (e.g., paclitaxel, docetaxel, ixabepilone, vinblastine, vincristine, vinorelbine, estramustine); corticosteroids (e.g., prednisone, methylprednisolone, dexamethasone); and the like. In certain embodiments, the chemotherapeutic agent is preferably a hydrophilic chemotherapeutic agent.

A "terminal group" is a chemical moiety that forms the terminus of a chemical polymer. can be any group known in the art that terminates a polymer. The terminal group may include a reactive functional group that allows conjugation of the chitosan polymer compounds described herein to other compounds, such as peptides, proteins, polysaccharides, and the like. Such conjugates may be synthesized using bioconjugate or conjugate chemistry. Conjugate chemistry includes coupling two molecules together to form an adduct. Conjugation may be a covalent modification. Currently favored classes of conjugate chemistry reactions available with reactive known reactive groups are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the bioconjugation reaction is a click chemistry reaction (Angewandte Chemie International Edition 40 (11): 2004-2021). In embodiments, the bioconjugation reaction is a Huisgen cyclization of azides. In embodiments, the bioconjugation reaction is a copper catalyzed Huisgen cyclization of azides.

Exemplary reactive functional groups used for bioconjugate or conjugate chemistries herein include, for example: (a) carboxyl groups and various derivatives thereof including, but not limited to, N-hydroxysuccinimide esters, N-hydroxybenzotriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc. (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold; (h) amine or sulfhydryl groups, which can be, for example, acylated, alkylated or oxidized; (i) alkenes, which can undergo, for example, cycloadditions, acylation, Michael addition, etc; (j) epoxides, which can react with, for example, amines and hydroxyl compounds; (k) phosphoramidites and other standard functional groups useful in nucleic acid synthesis; (l) metal silicon oxide bonding; and (m) metal bonding to reactive phosphorus groups (e.g. phosphines) to form, for example, phosphate diester bonds. (n) azides coupled to alkynes using copper catalyzed cycloaddition click chemistry. The reactive functional groups can be chosen such that they do not participate in, or interfere with, the chemical stability of the conjugate described herein. Alternatively, a reactive functional group can be protected from participating in the crosslinking reaction by the presence of a protecting group.

Other exemplary Terminal Groups include chemical groups (e.g., amine, thiol, hydroxyl, azide, carboxyl); polymerizable groups (e.g., acrylate, methacrylate, alkene); reactive groups (e.g., NHS, maleimide, isocyanate, vinyl sulphone); biotin; fluorophores; contrast agents; radio isotopes; enzymes (e.g., proteases (e.g., cathepsin B, CAPs, PSA), lipases (e.g., PLA), glycosidases (e.g., amilase), urease, glucose oxidase, peroxidase, esterase, amidase); cell-penetrating peptides; targeting peptides; targeting antibodies; intracellular localization signals; anti-microbial peptides; poly(NIPAM-acrylamide); poly(NIPAM-vinylpyrrolidone); poly(methylvinylether); poly(N-vinylcaprolactam); gold nanoshell; nanorods; silver; titanium dioxide; fullerene; gold; zinc oxide; polyethylene glycol; gelatin; dextran; collagen; glucose; galactose; fructose; glucoronic acid; xylose; mannose; DNA; RNA (e.g., dsRNA, siRNA, shrRNA, crRNA); peptide nucleic acid; glycol nucleic acid; acetyl; phthalyl; methoxy; hydroxypropoxy; succinyl; carboxymethyl; imine; amino ester; ketal; polyhistidine; hydrazone; hydrazide; oxime; acetal; dimethyl maleate; disulfide; azobenzene; nitroaromatic; and quinone. In embodiments, the terminal group is hydrogen, —OH, —COOH, —CONH2, —COH, —C(O)CH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The term "treat", "treating" or "treatment" as used herein refers to administering a compound or pharmaceutical composition for prophylactic and/or therapeutic purposes. The term "prophylactic treatment" refers to treating a subject who is not yet infected, but who is susceptible to, or otherwise at a risk of infection (preventing the bacterial infection). The term "therapeutic treatment" refers to administering treatment to a subject already suffering from infection.

The terms "treat", "treating" or "treatment" a bacterial infection as used herein also refer to administering the compounds or pharmaceutical compositions described herein, with or without additional pharmaceutically active or inert ingredients, in order to: (i) reduce or eliminate either a bacterial infection or one or more symptoms of the bacterial infection, or (ii) retard the progression of a bacterial infection one or more symptoms of the bacterial infection, or (iii) reduce the severity of a bacterial infection or of one or more symptoms of the bacterial infection, or (iv) suppress the clinical manifestation of a bacterial infection, or (v) suppress the manifestation of adverse symptoms of the bacterial infection.

"Pharmaceutically acceptable excipient" refers to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

"Subject" or "subject in need thereof" refers to a living organism suffering from or prone to a disease or condition that can be treated by administration of a composition or pharmaceutical composition as provided herein. Non-limiting examples of a subject include humans, pets, domesticated animals, and zoo animals. In some embodiments, a subject is a human.

Provided herein are polymeric compounds of Formula (I):

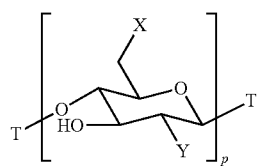

Formula (I)

wherein each Y is independently —NH$_2$, —NH—C(=O)CH$_3$, or a protecting group; each X is independently —OH, —O—C(R$^1$R$^2$)—O—(CH$_2$—CH$_2$—O)$_x$—(CH$_2$)$_y$—R$^3$, or —O—C(R$^1$R$^2$)—O-D; provided, however, that at least one X is not —OH; p is 2 or more; x and y are each independently an integer from 1 to 10; each T is independently a terminal group; R$^1$ and R$^2$ are each independently H, a substituted C$_{1-6}$ alkyl group, an unsubstituted C$_{1-6}$ alkyl group, a substituted C$_{5-6}$ heteroalkyl group, or an unsubstituted C$_{5-6}$ heteroalkyl group; R$^3$ is —NH$_2$, —C(=O)—R$^4$, or —NH$_2$—C(=O)—R$^4$; and R$_4$ is D, a C$_{1-6}$ alkyl group, or a C$_{1-6}$ alkyl group substituted with one or more halogen atoms; and D is a drug moiety. In embodiments, R$^1$ and R$^2$ are each independently H, a substituted C$_{1-4}$ alkyl group, an unsubstituted C$_{1-4}$ alkyl group, a substituted C$_{5-6}$ heteroalkyl group wherein the heteroatoms are nitrogen or oxygen, or an unsubstituted C$_{5-6}$ heteroalkyl group wherein the heteroatoms are nitrogen or oxygen. In embodiments, R$^1$ and R$^2$ are each independently H, a substituted C$_{1-3}$ alkyl group, or an unsubstituted C$_{1-3}$ alkyl group. In embodiments, R$^1$ and R$^2$ are each independently H, —CH$_3$ or —CH$_2$CH$_3$. In embodiments, R$^1$ and R$^2$ are each H. In embodiments, T is independently selected from hydrogen and —OH.

In embodiments of Formula (I), 10% to 100% of the Y in the polymeric compound are NH$_2$, and 0% to 90% of the Y in the polymeric compounds are —NH—C(=O)CH$_3$. In embodiments of Formula (I), 25% to 100% of the Y in the polymeric compound are NH$_2$, and 0% to 75% of the Y in the polymeric compounds are —NH—C(=O)CH$_3$. In embodiments of Formula (I), 50% to 100% of the Y in the polymeric compound are NH$_2$, and 0% to 50% of the Y in the polymeric compounds are —NH—C(=O)CH$_3$. In embodiments of Formula (I), 75% to 100% of the Y in the polymeric compound are NH$_2$, and 0% to 25% of the Y in the polymeric compounds are —NH—C(=O)CH$_3$. In embodiments of Formula (I), 85% to 100% of the Y in the polymeric compound are NH$_2$, and 0% to 15% of the Y in the polymeric compounds are —NH—C(=O)CH$_3$. In other embodiments of Formula (I), 80% to 90% of the Y in the polymeric compound are NH$_2$, and 10% to 20% of the Y in the polymeric compounds are —NH—C(=O)CH$_3$.

In embodiments of Formula (I), each X is independently —OH, —O—C(R$^1$R$^2$)—O—(CH$_2$—CH$_2$—O)$_x$—(CH$_2$)$_y$—R$^3$, or —O—C(R$^1$R$^2$)—O-D, provided that 10% to 100% of the X are not —OH; or 25% to 100% of the X are not —OH; or 50% to 100% of the X are not —OH; or 80% to 100% of the X are not —OH; or 90% to 100% of the X are not —OH. In another embodiment, 25% to 90% of the X are not —OH; or 50% to 90% of the X are not —OH; or 75% to 90% of the X are not —OH.

In embodiments of Formula (I), each X is independently —OH or —O—C(R$^1$R$^2$)—O—(CH$_2$—CH$_2$—O)$_x$—(CH$_2$)$_y$—R$^3$; provided that 10% to 100% of the X are not —OH. In this embodiment, each R$^1$ and R$^2$ are independently a hydrogen atom, C$_{1-4}$ alkyl group, or a C$_{5-6}$ heteroalkyl group; or each R$^1$ and R$^2$ are independently a hydrogen atom or a C$_{1-4}$ alkyl group; or each R$^1$ and R$^2$ are independently a hydrogen atom or a C$_{1-2}$ alkyl group; or each R$^1$ and R$^2$ are a hydrogen atom. In this embodiment, x and y are each independently an integer from 1 to 8; or x and y are each independently an integer from 1 to 6; or x and y are each independently an integer from 1 to 5; or x and y are each independently an integer from 1 to 4; or x and y are each independently an integer from 1 to 3. In other embodiments, each x is independently an integer from 1 to 3 and each y is 1. In other embodiments, x is 3 and y is 1. In other embodiments, x is 2 and y is 1. In other embodiments, x is 1 and y is 1. In embodiments, R$^3$ is —NH$_2$. In embodiments, R$^3$ is —C(=O)—R$^4$ and R$^4$ is an antibiotic. In embodiments, R$^3$ is —NH$_2$—C(=O)—R$^4$ and R$^4$ is an antibiotic. In embodiments, R$^3$ is —C(=O)—R$^4$ and R$^4$ is a C$_{1-4}$ alkyl group. In embodiments, R$^3$ is —NH$_2$—C(=O)—R$^4$ and R$^4$ is a C$_{1-4}$ alkyl group. In embodiments, R$^3$ is —C(=O)—R$^4$ and R$^4$ is a C$_{1-2}$ alkyl group substituted with one or more fluorine atoms. In embodiments, R$^3$ is —NH$_2$—C(=O)—R$^4$ and R$^4$ is a C$_{1-4}$ alkyl group substituted with one or more fluorine atoms. In embodiments, R$^3$ is —C(=O)—CF$_3$. In embodiments, R$^3$ is —NH$_2$—C(=O)—CF$_3$.

In embodiments of Formula (I), each X is independently —OH or —O—C(R$^1$R$^2$)—O-D; provided that 10% to 100% of the X are not —OH. In this embodiment, each R$^1$ and R$^2$ are independently a hydrogen atom, C$_{1-4}$ alkyl group, or a C$_{5-6}$ heteroalkyl group; or each R$^1$ and R$^2$ are independently a hydrogen atom or a C$_{1-4}$ alkyl group; or each R$^1$ and R$^2$ are independently a hydrogen atom or a C$_{1-2}$ alkyl group; or each R$^1$ and R$^2$ are a hydrogen atom. In embodiments, D is an antibiotic. In embodiments, D is a chemotherapeutic agent. In embodiments, D is a tuberculosis drug.

In embodiments of Formula (I), each terminal group (T) is independently selected from hydrogen and —OH. In embodiments of Formula (I), each terminal group (T) is independently selected from hydrogen, —OH, 3-amino-6-(hydroxymethyl)-5-(λ$^1$-oxidanyl)tetrahydro-2H-pyran-2,4-diol, and 5-amino-2-(hydroxymethyl)tetrahydro-2H-pyran-3,4-diol-6-yl. In embodiments of Formula (I), T may comprise a solid support. The term "3-amino-6-(hydroxymethyl)-5-(λ$^1$-oxidanyl)tetrahydro-2H-pyran-2,4-diol" refers to the chemical structure:

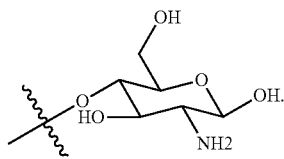 [SMILES: *OC1C(CO)OC(O)C(N)C1O]

The term "5-amino-2-(hydroxymethyl)tetrahydro-2H-pyran-3,4-diol-6-yl" refers to the chemical structure:

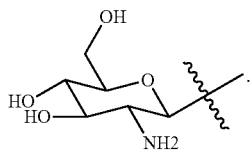 [SMILES: *C1OC(CO)C(O)C(O)C1N]

In other embodiments of Formula (I), T is reactive functional group as described and defined herein.

In Formula (I), p is an integer of at least 2 that provides for a polymeric compound of chitosan. In one aspect, p is an integer that provides for a polymeric compound of Formula (I) having a molecular weight from about 50 to about 1,000,000; or from about 100 to about 500,000; or from about 500 to about 100,000; or from about 1,000 to about 50,000; or from about 3,000 to about 20,000. In one aspect, p is an integer of 2 to 1,000; or an integer of 2 to 500; or an integer of 2 to 300; or an integer of 4 to 200.

When Y is a protecting group in Formula (I), the protecting group can be any known in the art. In embodiments, the protecting group is an amine protecting group. In embodiments, the protecting group is 9-fluorenylmethyl carbamate (FMOC), t-butyl carbamate (BOC), benzyl carbamate, acetamide, trifluoroacetamide, phthalimide, benzylamine, triphenylmethylamine, benzylideneamine, p-toluenesulfonamide, or tosylamide. In embodiments, the protecting group is phthalimide. In embodiments of Formula (I), 25% to 100% of the Y in the polymeric compound are a protecting group; 0% to 25% of the Y in the polymeric compound are —NH$_2$; and 0% to 75% of the Y in the polymeric compounds are —NH—C(=O)CH$_3$.

Provided herein are polymeric compounds of Formula (IA):

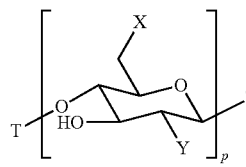

Formula (IA)

wherein each Y is independently —NH$_2$, —NH—C(=O)—CH$_3$, or a protecting group; each X is independently a hydroxyl group, an unsubstituted alkoxy group, or a substituted alkoxy group; provided, however, that at least one X is not a hydroxyl group; p is 2 or more; x and y are each independently an integer from 1 to 25; each T is independently a terminal group. In embodiments, T is independently selected from hydrogen and —OH.

Provided herein are polymeric compounds of Formula (IB):

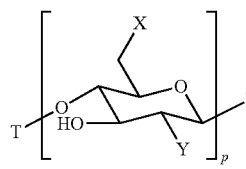

Formula (IB)

wherein each Y is independently —NH$_2$, —NH—C(=O)CH$_3$, or a protecting group; each X is independently —OH, —O—C(R$^1$R$^2$)—O—(CH$_2$—CH$_2$—O)$_x$—(CH$_2$)$_y$—R$^3$, —O—S(R$^1$R$^2$)—O—(CH$_2$—CH$_2$—O)$_x$—(CH$_2$)$_y$—R$^3$, —S—C(R$^1$R$^2$)—S—(CH$_2$—CH$_2$—O)$_x$—(CH$_2$)$_y$—R$^3$, —O—C(R$^1$R$^2$)—O-D, —S—C(R$^1$R$^2$)—S-D, or —O—S(R$^1$R$^2$)—O-D; provided, however, that at least one X is not —OH; p is 2 or more; x and y are each independently an integer from 1 to 20; each T is independently a terminal group; R$^1$ and R$^2$ are each independently H, a substituted alkyl group, an unsubstituted alkyl group, a substituted heteroalkyl group, or an unsubstituted heteroalkyl group; R$^3$ is —NH$_2$, —C(=O)—R$^4$, or —NH$_2$—C(=O)—R$^4$; and R$_4$ is D, an alkyl group, or a substituted alkyl group; and D is a drug moiety. In embodiments, each X is independently —OH, —O—C(R$^1$R$^2$)—O—(CH$_2$—CH$_2$—O)$_x$—(CH$_2$)$_y$—R$^3$, or —O—C(R$^1$R$^2$)—O-D; provided, however, that at least one X is not —OH. In embodiments, T is independently selected from hydrogen and —OH.

Provided herein are polymeric compounds of Formula (IC):

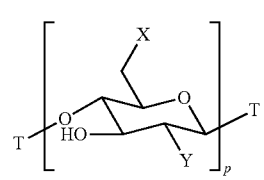

Formula (IC)

wherein each Y is independently —NH$_2$, —NH—C(=O)CH$_3$, or a protecting group; each X is independently —OH, —O—S(R$^1$R$^2$)—O—(CH$_2$—CH$_2$—O)$_x$—(CH$_2$)$_y$—R$^3$, —S—C(R$^1$R$^2$)—S—(CH$_2$—CH$_2$—O)$_x$—(CH$_2$)$_y$—R$^3$, —O—S(R$^1$R$^2$)—O-D, or —S—C(R$^1$R$^2$)—S-D; provided, however, that at least one X is not —OH; p is 2 or more; x and y are each independently an integer from 1 to 10; each T is independently a terminal group; R$^1$ and R$^2$ are each independently H, a substituted C$_{1-6}$ alkyl group, an unsubstituted C$_{1-6}$ alkyl group, a substituted C$_{5-6}$ heteroalkyl group, or an unsubstituted C$_{5-6}$ heteroalkyl group; R$^3$ is —NH$_2$, —C(=O)—R$^4$, or —NH$_2$—C(=O)—R$^4$; and R$_4$ is D, a C$_{1-6}$ alkyl group, or a C$_{1-6}$ alkyl group substituted with one or more halogen atoms; and D is a drug moiety. In embodiments, R$^1$ and R$^2$ are each independently H, a substituted C$_{1-4}$ alkyl group, an unsubstituted C$_{1-4}$ alkyl group, a substituted C$_{5-6}$ heteroalkyl group wherein the heteroatoms are nitrogen or oxygen, or an unsubstituted C$_{5-6}$ heteroalkyl group wherein the heteroatoms are nitrogen or oxygen. In embodiments, R$^1$ and R$^2$ are each independently H, a substituted C$_{1-3}$ alkyl group, or an unsubstituted C$_{1-3}$ alkyl group. In embodiments, each X is independently —OH, —S—C(R$^1$R$^2$)—S—(CH$_2$—CH$_2$—O)$_x$—(CH$_2$)$_y$—R$^3$, or —S—C(R$^1$R$^2$)—S-D.

Provided herein are polymeric compounds of Formula (II):

A-(L-B)$_p$    Formula (II)

wherein A is chitosan; L is a cleavable linking group; B is a drug, a hydrophilic group, or a hydrophilic group linked to a drug; and p is an integer greater than 2.

In Formula (II), the chitosan comprises from 25% to 100% deacetylated monomers and 0% to 75% acetylated monomers; or from 50% to 100% deacetylated monomers and from 0% to 50% acetylated monomers; or from 80% to 100% deacetylated monomers and from 0% to 20% acetylated monomers.

In Formula (II), L can be any cleavable linking group known in the art. A "cleavable linking group" refers to a chemical linking group which can be stable in vitro or in vivo but which can cleave upon entry into a target cell or under exposure to a cleaving agent, thereby releasing the moieties linked by the cleavable linking group. A "cleaving agent" refers to a physiological or non-physiological chemical agent or condition which is capable of chemically cleaving a cleavable linking group. For example, cleavage agents include pH, redox potential, degradative agent including esterases, proteases, nucleases, amylases, lipases, and the like. In embodiments, cleavage agents can be found in higher concentration inside cells relative to serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases. The cleavable linking group can be a physiologically cleavable ester or physiologically hydrolysable ester which is a substrate for a carboxyesterases in vivo. These esters are typically formed from the reaction of a corresponding carboxylic acid (X—$CO_2H$) or an alcohol (X—OH), respectively, with a compound, e.g., a compound disclosed herein, which provides an alcohol or acid functionalities, respectively. X can be a substituted or unsubstituted alkyl, a ($C_1$-$C_3$)alkyl, a ($C_1$ to $C_6$)alkyl (e.g., ethyl), aryl, heteroaryl, cycloalkyl, or heterocycloalkyl function. In embodiments, a pharmaceutically acceptable alcohols and acids are contemplated (e.g., ethanol, benzoic acid, and the like). In embodiments, functional groups useful in the composition of cleavable linker groups include: carboxyl groups and derivatives thereof including, but not limited to, N-hydroxysuccinimide esters, N-hydroxybenzotriazole esters, acid halides, acyl imidazoles, thioesters, p-nitrophenyl esters, alkyl, alkenyl, alkynyl and aromatic esters; hydroxyl groups which can be converted to esters, ethers, aldehydes, etc.; haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; dienophile groups which are capable of participating in Diels-Alder reactions such as, for example, maleimido groups; aldehyde or ketone groups such that subsequent derivatization is possible via formation of carbonyl derivatives such as, for example, imines, hydrazones, semicarbazones or oximes, or via such mechanisms as Grignard addition or alkyllithium addition; sulfonyl halide groups for subsequent reaction with amines, for example, to form sulfonamides; thiol groups, which can be converted to disulfides, reacted with acyl halides, or bonded to metals; amine or sulfhydryl groups, which can be, for example, acylated, alkylated or oxidized; alkenes, which can undergo, for example, cycloadditions, acylation, Michael addition, and the like; epoxides, which can react with, for example, amines and hydroxyl compounds; phosphoramidites and other standard functional groups useful in nucleic acid synthesis; and metal bonding to reactive phosphorus groups (e.g. phosphines) to form, for example, phosphate diester bonds. In embodiments, the cleavage site is an amino acid sequence that is recognized and cleaved by a cleavage agent (e.g. a peptidyl sequence). Exemplary cleavage agents include proteins, enzymes, DNAzymes, RNAzymes, metals, acids, and bases.

In Formula (II), when B is a drug or when the drug is linked to a hydrophilic group, the drug can be any known in the art. In embodiments, the drug is an antibiotic. In embodiments, the drug is a chemotherapeutic agent. In embodiments, the drug is a tuberculosis drug.

When B contains a hydrophilic group, either alone or linked to a drug, the hydrophilic group can be any known in the art. Exemplary hydrophilic groups include alkoxy groups (e.g., methoxy, ethoxy, propoxy); hydroxyl groups (e.g., alcohols and sugars), carbonyl groups (e.g., aldehydes and ketones), carboxyl groups (e.g., carboxylic acids), amino groups (e.g., amino acids), sulfhydryl groups, phosphate groups, ether groups, ester groups, and phosphodiester groups. In embodiments, the hydrophilic group includes a methoxy functionality. In embodiments, hydrophilic group includes an ethoxy functionality. In embodiments, hydrophilic group includes a propoxy functionality. In embodiments, hydrophilic group includes a hydroxyl group in an alcohol, e.g., hydroxylalkyl, hydroxyheteroalkyl, hydroxycycloalkyl, hydroxyheterocycloalkyl, hydroxyaryl, hydroxyheteroaryl, and the like. In embodiments, hydrophilic group includes a sugar or derivative thereof (e.g., a chitosan derivative disclosed herein). In embodiments, hydrophilic group includes a carbonyl group, e.g., alkylcarbonyl, heteroalkylcarbonyl, cycloalkylcarbonyl, heterocyclocarbonyl, arylcarbonyl, heteroarylcarbonyl, and the like. In embodiments, hydrophilic group includes a ketone group, e.g., alkylketone, heteroalkylketone, cycloalkylketone, heterocycloketone, arylketone, heteroarylketone, and the like. In embodiments, hydrophilic group includes a carboxyl group, e.g., alkyl carboxylic acid, heteroalkyl carboxylic acid, cycloalkyl carboxylic acid, heterocycloalkyl carboxylic acid, aryl carboxylic acid, heteroaryl carboxylic acid, and the like. In embodiments, hydrophilic group includes an amino functionality, e.g., alkyl amine, heteroaryl amine, cycloalkyl amine, heterocycloalkyl amine, aryl amine, heteroaryl amine, and the like. In embodiments, hydrophilic group includes an amino functionality and a carboxyl functionality, e.g., a physiological or non-physiological amino acid. In embodiments, hydrophilic group includes a sulfhydryl functionality, e.g., alkyl thiol, heteroaryl thiol, cycloalkyl thiol, heterocycloalkyl thiol, aryl thiol, heteroaryl thiol, and the like. In embodiments, hydrophilic group includes a phosphate functionality, e.g., alkyl phosphate, heteroalkyl phosphate, cycloalkyl phosphate, hetero cycloalkyl phosphate, aryl phosphate, hetero aryl phosphate, and the like. In embodiments, hydrophilic group includes an ether functionality. In embodiments, hydrophilic group includes an ester functionality. In embodiments, hydrophilic group includes a phosphodiester functionality.

In Formula (II), p is an integer of at least 2 that provides for polymeric compound or chitosan. In one aspect, p is an integer that provides for a polymeric compound of Formula (II) having a molecular weight from about 50 to about 1,000,000; or from about 100 to about 500,000; or from about 500 to about 100,000; or from about 1,000 to about 50,000; or from about 3,000 to about 20,000. In one aspect, p is an integer of 2 to 1,000; or an integer of 2 to 500; or an integer of 2 to 300; or an integer of 4 to 200.

Provided herein are ketal-chitosans comprising the monomer of Formula (III):

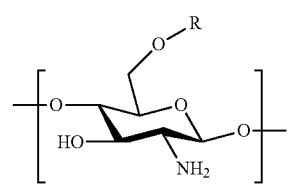

Formula (III)

wherein R is a optionally substituted heteroalkyl moiety forming a ketal with the chitosan monomer. In embodiments, R is —CH$_2$—O—(CH$_2$—CH$_2$—O)$_x$—(CH$_2$)$_y$—R$^3$, where x and y are each independently an integer from 1 to 10; R$^3$ is —NH$_2$, —C(=O)—R$^4$, or —NH$_2$—C(=O)—R$^4$; and R$_4$ is D, a C$_{1-6}$ alkyl group, or a C$_{1-6}$ alkyl group substituted with one or more halogen atoms; and D is a drug.

Provided herein are pharmaceutical compositions comprising the compounds described herein and a pharmaceutically acceptable excipient. The pharmaceutical composition may be prepared and administered in a wide variety of dosage formulations and may be administered orally, rectally, or by injection (e.g. intravenously, intramuscularly, intracutaneously, subcutaneously, intraduodenally, or intraperitoneally).

Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In tablets, the compounds described herein may be mixed with an excipient having the necessary binding properties in suitable proportions and compacted in the shape and size desired. Suitable excipients are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include a formulation of the recombinant proteins described herein with or without other carriers, and surrounded by a carrier, which is thus in association with it. Similarly, cachets and lozenges are included. Tablets, powders, capsules, pills, cachets, and lozenges can be used as solid dosage forms suitable for oral administration.

Liquid form preparations include solutions, suspensions, and emulsions, for example, water or water/propylene glycol solutions. For parenteral injection, liquid preparations can be formulated in solution in aqueous polyethylene glycol solution. Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents. The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

The pharmaceutical preparation is preferably in unit dosage form. In such form the preparation is subdivided into unit doses containing appropriate quantities of the compositions described herein. The unit dosage form can be a packaged preparation, the package containing discrete quantities of preparation, such as packeted tablets, capsules, and powders in vials or ampoules.

The pharmaceutical composition may include compositions wherein the therapeutic agent is contained in a therapeutically effective amount, i.e., in an amount effective to achieve its intended purpose. The actual amount effective for a particular application will depend, inter alia, on the condition being treated. For example, when administered in methods to treat cancer, such compositions will contain amounts of therapeutic agent effective to achieve the desired result.

The dosage and frequency (single or multiple doses) of the pharmaceutical composition administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

In embodiments, the compounds, pharmaceutical compositions, and methods disclosed herein are useful in preventing or treating bacterial infections. Advantageously, the compositions and methods disclosed herein are also effective in preventing or treating infections caused by bacteria that are considered to be less or not susceptible to one or more of known antibacterial agents or their known compositions. Some non-limiting examples of such bacteria known to have developed resistance to various antibacterial agents include *Acinetobacter, E. coli, Pseudomonas aeruginosa, Staphylococcus aureus, Enterobacter, Klebsiella, Citrobacter*, and the like. Other non-limiting examples of infections that may be prevented or treated using the compositions and/or methods of the invention include skin and soft tissue infections, febrile neutropenia, urinary tract infection, intraabdominal infections, respiratory tract infections, pneumonia (nosocomial), bacteremia meningitis, surgical infections, and the like.

In embodiments, the compounds, pharmaceutical compositions, and methods disclosed herein are useful in preventing or treating cancer. The methods of treating cancer include, for example, delaying the progression of cancer; preventing the growth of cancer cells; and killing cancer cells.

In embodiments, the compounds, pharmaceutical compositions, and methods disclosed herein are useful in treating tuberculosis (including latent tuberculosis). The methods of treating tuberculosis include killing the tuberculosis-causing bacteria; preventing relapse of tuberculosis; reducing the transmission of tuberculosis; and preventing the development of drug-resistant tuberculosis bacteria. In addition to a compound herein that is useful to treat tuberculosis, a multi-drug regimen can be used, as is known in the art.

In another aspect there is provided a method for synthesis of the compounds described herein, the method including protecting a chitosan monomer, reacting the protected chitosan with a half acetal moiety under conditions suitable to form a protected ketal chitosan, and deprotecting the protected ketal chitosan, in order to afford a ketal chitosan. A representative schematic synthesis of compounds disclosed herein follows as Scheme 1. Scheme 1: Step 1: DMF with 5% H$_2$O, 120° C., 5-hr, N$_2$; Step 2: PPTS, sieves, N$_2$, overnight stirred; Step 3: 6M NaOH, 2-hr stirred; Step 4: hydrazine, 12-hr stirred. A further exemplary synthetic scheme is set forth in Scheme 2 following. Scheme 2: Step 1: DMA with 5% H$_2$O; Step 2: THF with PPTS; Step 3: 1 M NaOH, hydrazine.

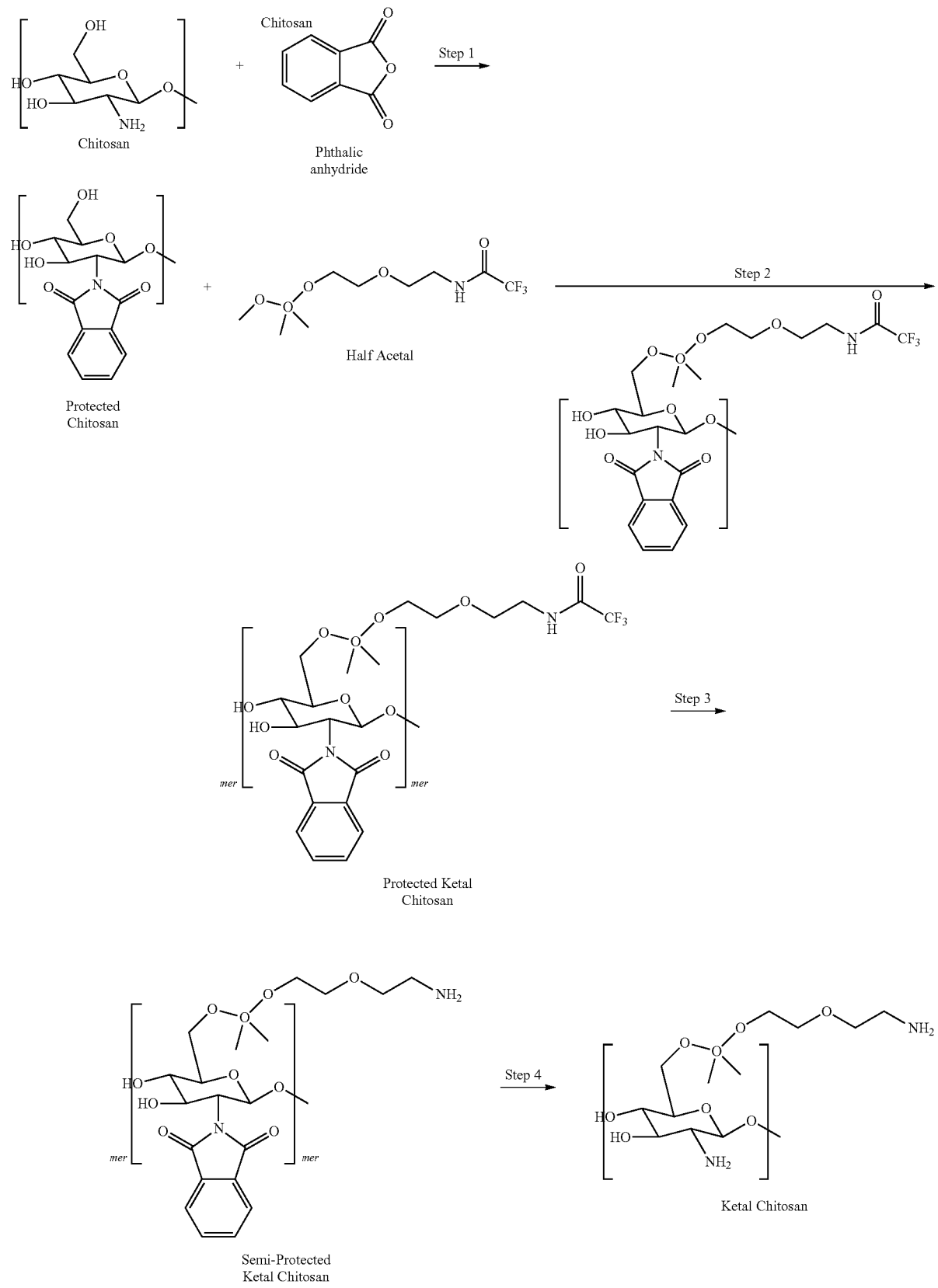

In embodiments, a method of synthesis of the compounds disclosed herein is provided in the following Scheme 2.

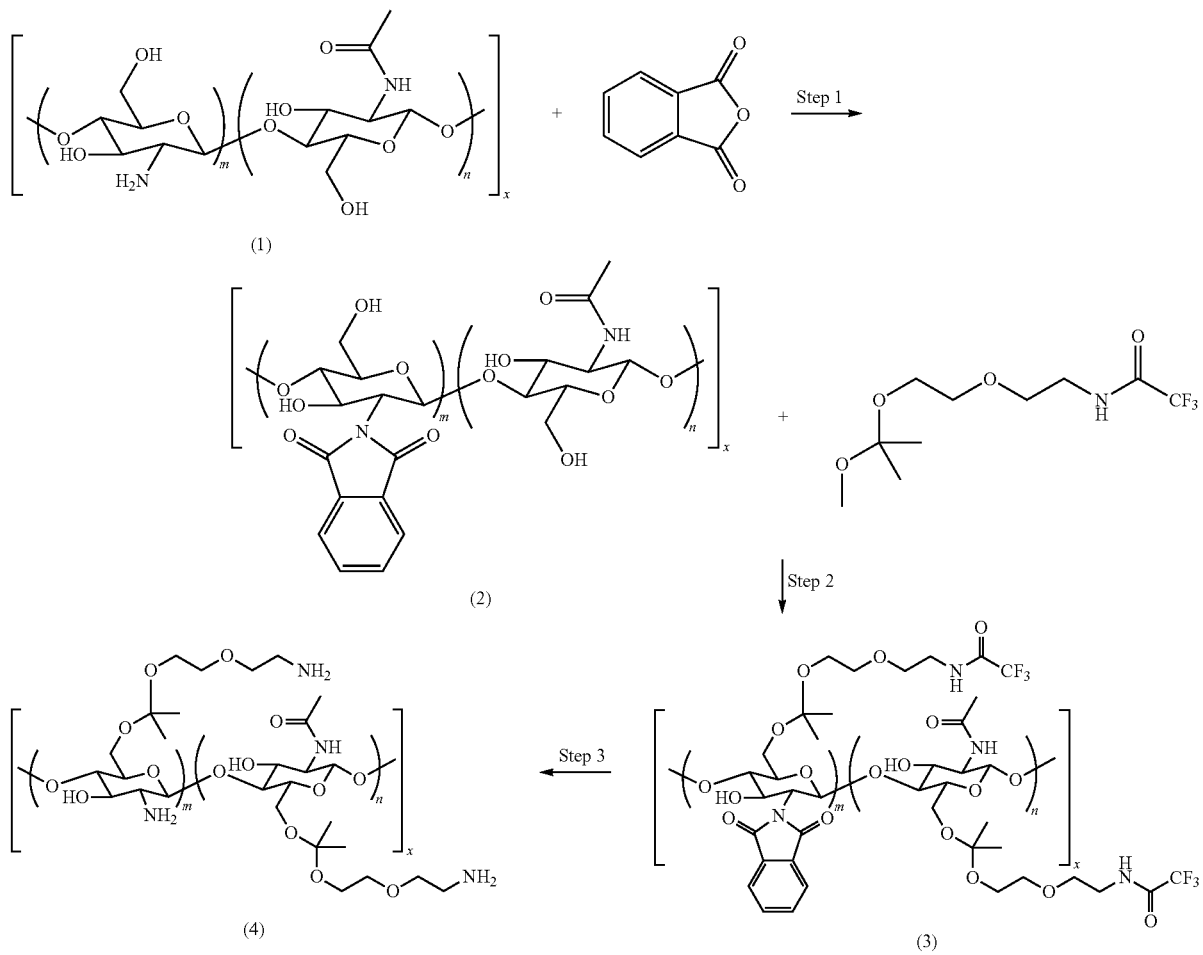

EXAMPLES

Materials and Methods

All chemicals were purchased from commercially available sources and used as received. Medium molecular weight chitosan was purchased from Sigma-Aldrich (St. Louis, Mo.) and used as received. The degree of deacetylation (DD) was 76% as determined by proton nuclear magnetic resonance (1H NMR), in D2O with 1% DCl as a solvent. Phthalic anhydride, dimethyl formaldehyde pyridinium p-toluenesulfonate (PPTS), 5 angstrom molecular sieves, triethylamine, tetrahydrofuran, methanol, ethanol, and hydrazine were purchased from Acros organics. 3-(4,5-dimethyl-2-thiazolyl)-2,5-diphenyltetrazolium bromide (MTT), were purchased from Sigma-Aldrich (St. Louis, Mo.). Plasmid DNA encoding enhanced green fluorescent protein (eGFP) (5.0 kbp) was a gift from Dr. Pamela Davis (Case Western Reserve University, Cleveland, Ohio). Silencer® GFP siRNA was purchased from Ambion (Austin, Tex., USA) and ethidium bromide was purchased from Fisher Scientific (Pittsburgh, Pa.). HeLa cells (ATCC, Rockville, Md.) were cultured in Dulbecco's modified Eagle's medium (DMEM) (MediaTech, Herndon, Va.) with 10% fetal bovine serum (FBS) (Hyclone, Logan, Utah) and 1% antibiotics (100 units mL-1 penicillin; 100 μg mL-1 streptomycin) (MediaTech).

Phthalamide Protection of Chitosan.

Medium molecular weight chitosan (1 g) and phthalic anhydride (4 g) were mixed in a 50 mL round bottom flask containing 30 mL dimethyl formaldehyde (DMF) with 5% deionized water, and heated to 120° C. under $N_2$ for 5 hours. Product is recovered by cooling the reaction and emptying contents into an ice water bath. Precipitates were recovered and washed in ethanol for 4 hours, followed by a wash in methanol for 24 hours. Finally, the precipitates were collected and put under reduced atmosphere for 4 hours until dried.

Reaction with Protected Half Acetal.

Protected chitosan (1 g), pyridinium p-toluenesulfonate (PPTS) (2 g) and half acetal (3 g), described in an earlier publication [1], are mixed in a 100 mL round bottom flask with 50 mL anhydrous tetrahydrofuran (THF) and 5 angstrom molecular sieves. The reaction ran for 3 hours, and was then quenched with 5 mL triethylamine. The precipitate was collected and washed three times with methanol to remove residual PPTS, and unreacted half acetal. The precipitate was placed under high vacuum for 3 hours to ensure all solvent is removed.

Deprotection of kChitosan.

Protected ketal chitosan (1 g) was added to 10 mL of 1M sodium hydroxide and stirred for 24 hours. Any precipitate generated was removed by centrifugation and the liquid fraction was reacted with 20 percent hydrazine in ethanol at 85 degrees Celsius for 12 hours to remove phthalamide group. Product was dialyzed using a dialysis cassette (10 k MWCO) in deionized water for 24 hours to remove any trace of hydrazine.

Polyplex Formation.

kChitosan polyplexes are made at N/P ratios of 1, 5, 10, 20, 50, 100, 200, and 400 from medium molecular weight ketal chitosan. 5 mg of kChitosan was dissolved in 250 ul of DI water. This stock solution was further diluted to get a final concentration of 0.2 ug/ul. The diluted solution was added to enhanced green fluorescence protein (eGFP) DNA (1 ug/ul) and siRNA (1.5 ug/ul) drop-wise, mixed, and incubated at room temperature for 30 minutes to form kChit/DNA and kChit/siRNA polyplexes at weight ratio of 1:1 to 400:1. Polyplexes formed are then characterized.

Gel Retardation Assay.

The complexation efficiency of nucleic acid with kChitosan was determined by 1% agarose gel electrophoresis containing 5 μg/ml ethidium bromide. Polyplex at different ratios were loaded (18 μl of the sample with 2 μl (6×) loading dye) into each well and electrophoresis was carried out at a constant voltage of 45 V for 10 minutes then 100 V for 30 minutes in Tris-acetate-EDTA (TAE) buffer. Bands were then visualized under a UV transilluminator at a wavelength of 365 nm.

Transfection.

Polyplexes are transfected into HeLa cells seeded in a 24 well plate at 20,000 cells/well. 100 uL of polyplex solution was diluted with 300 uL of 1× phosphate buffered saline (PBS) before it was added to the wells. The particles incubate in the wells for 4 hours without any serum. After 4 hours of transfection, the medium was removed and the cells were washed with PBS, following this, media was replaced with 400 μL of Dulbecco's Modified Eagle's Medium (DMEM) with 10% fetal bovine serum (FBS) and incubated at 37° C. with a 5% $CO_2$ atmosphere for 24 or 48 hour. Analysis was performed 24 and 48 hours after transfection.

Cytotoxicity Assay.

Cytotoxicity of kChitosan was measured by determining cell viability of kChitosan/DNA polyplexes. HeLa cells were seeded in a 96-well plate at a density of 9,000 cells per well in DMEM with 10% of FBS and grown overnight. After 24 hours incubation of kChitosan/DNA polyplexes at 37° C., 20 μL (10% v/v) of MTT (3-(4,5-dimethyl-thiazol-2-yl)-2,5-diphenyl-tetrazolium bromide) (1 mg/ml) in serum free DMEM (200 μL) was added to each well and then incubated for 4 hours to allow formation of formazan crystals. After 4 hours, the unreduced MTT and medium was removed and the cells were washed with PBS. 200 μL of DMSO was then added to each well to dissolve the MTT formazan crystals and the plate was incubated at 37° C. for 5 min. The absorbance of formazan products was then measured at 540 nm Characterization.

Proton nuclear magnetic resonance ($^1$H NMR) was recorded on Bruker Advance II-400 MHz spectrometer in DMSO-$d_6$ and $D_2O/DCl$. Fourier transform infrared (FTIR) spectra were obtained on Jasco 4700 FTIR spectrophotometer between 4000 and 600 $cm^{-1}$ with resolution of 4 $cm^{-1}$. Sizes and zeta potentials of polyplexes were measured with a Zetasizer Nano ZS (Malvern, UK) at 25° C. and angle of 90°. Absorbance and fluorescence were measured on a BioTEK Synergy HT plate reader. Fluorescence activated cell sorting (FACS) measurements were done on a Guava Easycyte Plus. Transmission electron microscopy (TEM) images were taken on formvar carbon coated copper grids. The grids were imaged with a Philips/FEI CM-20 Transmission Electron Microscope operated at 200 kV.

Results

Analysis.

To confirm the formation of ketal chitosan, proton NMR was collected at the various steps in synthesis to determine the progress of modification. The appearance of the half acetal peak at 1.2 ppm and disappearance of the phthalamide peak at 7.8 ppm is indicative of a deprotected final kChitosan. When immersed in acidic solution from the nmr we can observe the transformation of the product from kChitosan back to Chitosan. IR characterization was obtained.

Particle Size and Transfection Efficiency Optimization.

kChitosan was then used to form polyplexes with egfp plasmid and egfp siRNA to determine the complexation capability of the material. Particle size of kChitosan/DNA or kChitosan/siRNA polyplexes, prepared by simple complexation, were characterized. kChit/DNA particle size increased gradually from an N/P ratio of 10 to 200 in distilled water (FIGS. 1A-1F). However, there is a slight decrease in PDI from N/P ratio of 10 to 100. Smallest particle sizes of kChit/DNA polyplexes were obtained at N/P ratios 20 and 100. kChit/siRNA polyplex size continue to gradually increase from N/P ratio of 10 to 200. Similarly, the PDI of the particles show a similar trend, with PDI of N/P ratio of 20 not following the same trend. The PDI of all the N/P ratios did not exceed 0.25 indicating low polydispersity of the particle sizes.

The zeta potential of kChit/DNA and kChit/siRNA polyplexes increased with the increasing concentration of kChitosan at a constant nucleic acid concentration. Without wishing to be bound by any theory, it is believed that the increment was due to the increase in the number of positive charges provided by kChitosan which counteracts with fixed negatively charged nucleic acid.

Figure 2A:
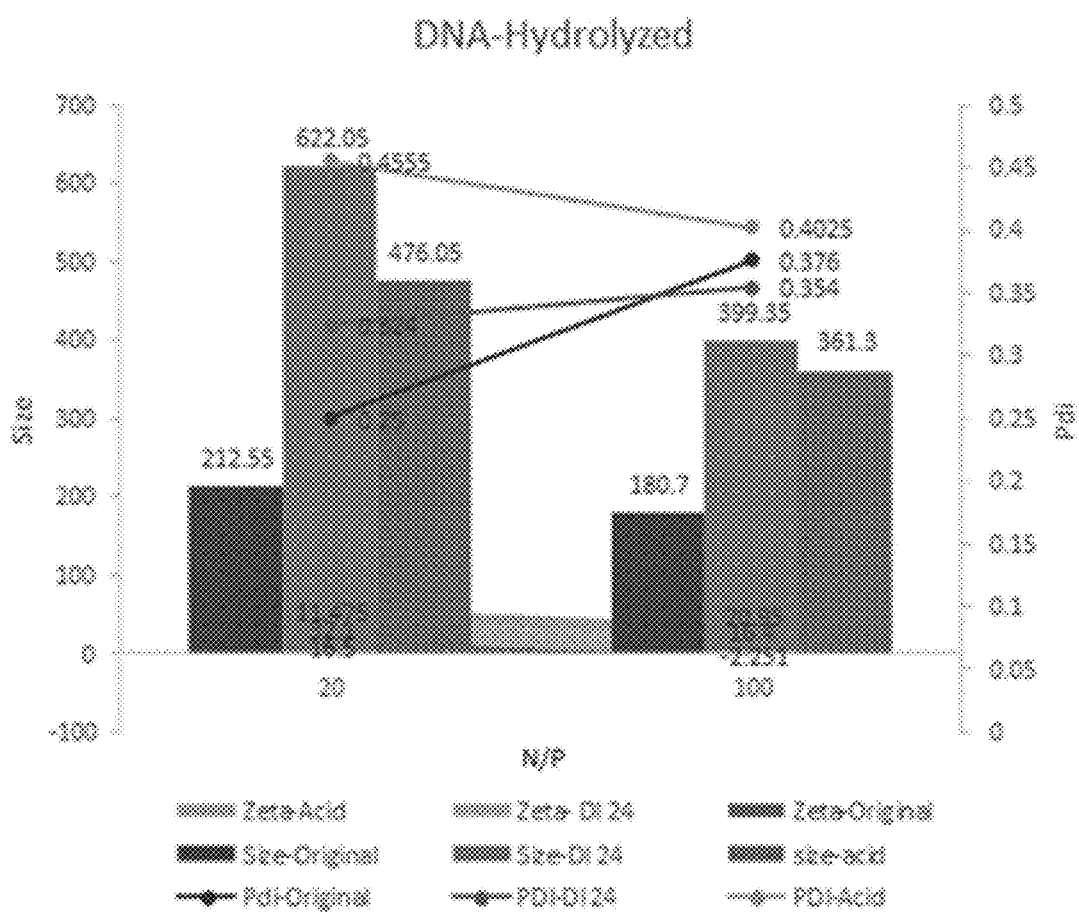
FIGS. 2A-2B.
Figure 2B:
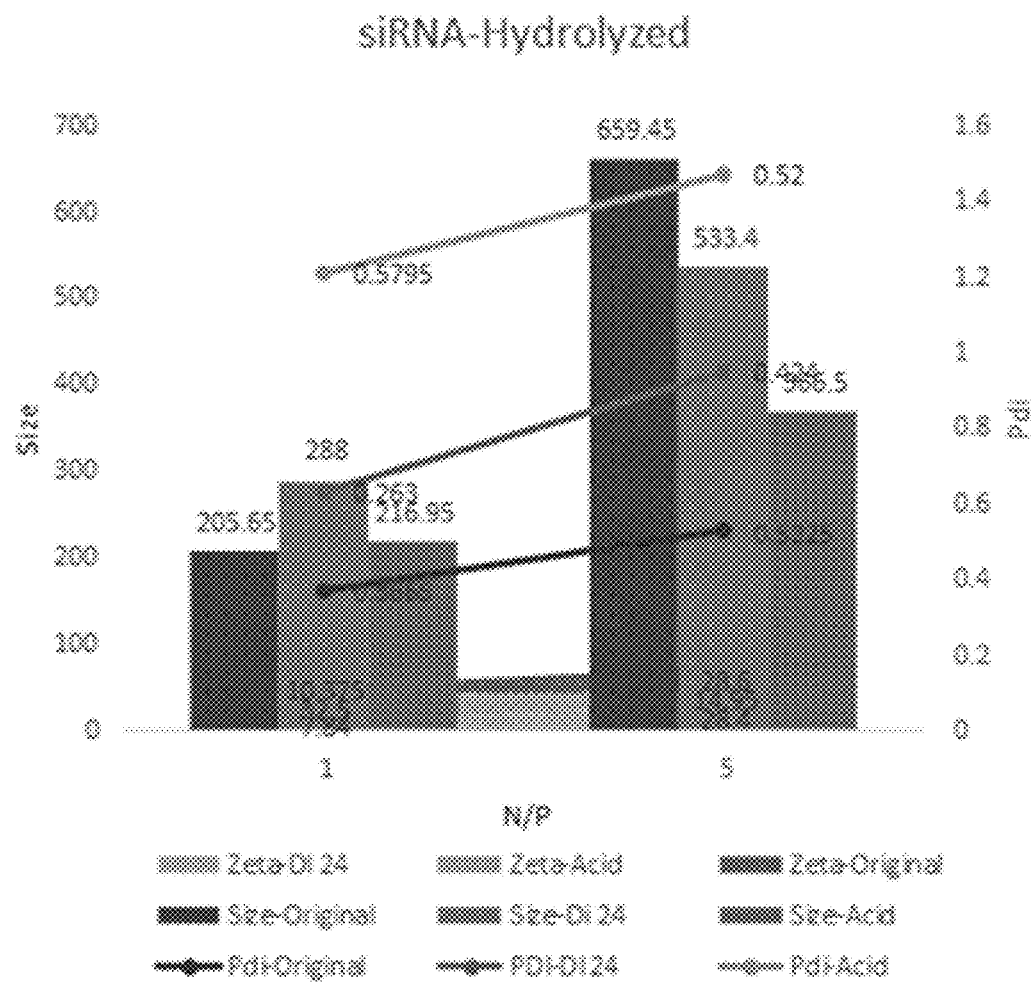

The change in the structure of the material can be observed in the modification of the particle size and charge. See FIGS. 2A-2B.

Metamorphic Capabilities.

Examining the gel electrophoresis, and transmission electron micrograph, the metamorphic capabilities of the material can be observed. At varying pH the material changes. In neutral pH, kChitosan complexes nucleic acid present in the solution adequately. In acidic pH the nucleic acids are release but some remain complexed due to kChitosan transforming to native chitosan, which is now soluble in the acid environment. In basic pH, native chitosan is no longer soluble and completely releases the nucleic acid.

FIG. 3 demonstrates that free nucleic acid reassemble into a polyplex with chitosan at pH 5. When returned to pH 8 there is release of all the nucleic acids except at N/P of 100. Additionally, in FIG. 3, conditions at pH 7 kChitosan and N/P of 20 to 100 effectively complexes DNA. At N/P ratios of 1 to 10 there is not enough polymer available to complex all the DNA in the solution, but some are still available to form a polyplex.

FIGS. 4A-4C demonstrate the variety of morphology available for kChitosan polyplexes. For example, the morphology and complexation efficiency of kChitosan polyplexes is observed using TEM and gel retardation assay respectively. In FIG. 4A, unmodified chitosan/DNA polyplexes form cubic structures with defined edges. When a polyplex is formed with kChitosan, a rough spherical object is created with various contusions. See FIG. 4B. By adding 100 nM acetic acid to the polyplex, hydrolysis of the ketal group occurs, causing kChitosan to revert to native chitosan. See FIG. 4C. When this occurs there is release of nucleic acid, but additionally the amine functionality on native chitosan becomes protonated as well.

In Vitro Studies.

Figure 5:
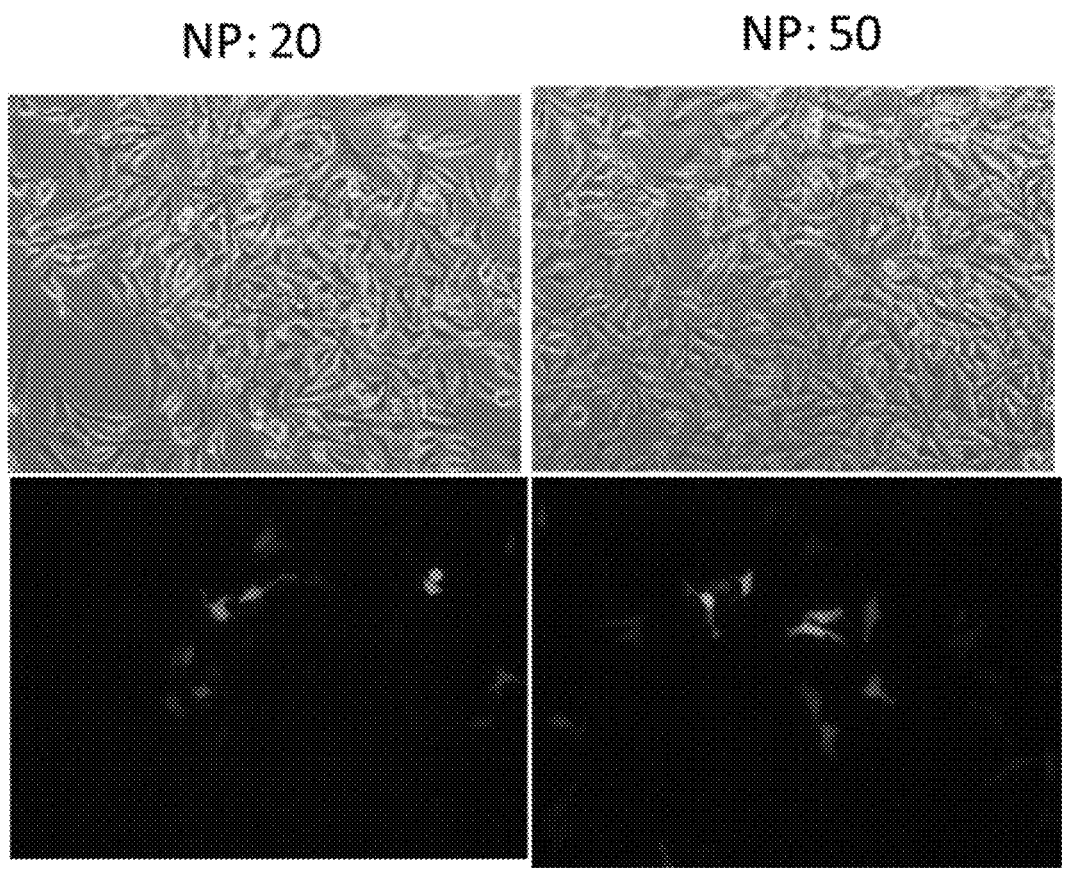
FIG. 5. Micrographs illustrating effective gene delivery and silencing capabilities of compounds disclosed herein. Left column: NP:20; right column: NP:50. Fluorescence images observed after 24-hr transfection of kChit/DNA plasmid on HeLa cells.
Figure 6A:
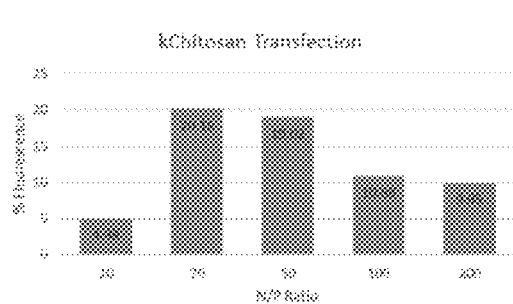
FIGS. 6A-6B. Fluorescence assay of kChitosan transfection as a function of N/P ratio (FIG. 6A), and % (GFP Expression) to demonstrate kChitosan silencing as a function of N/P ratio.
Figure 6B:
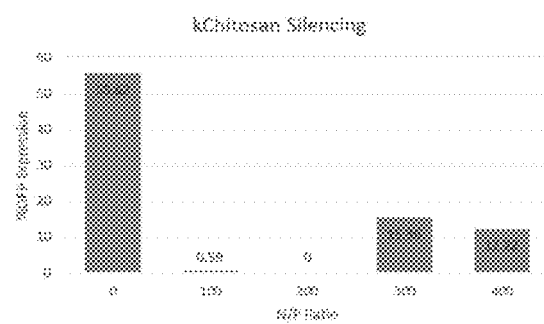

In Vitro studies indicate effective gene delivery and silencing capabilities, while maintaining low toxicity. Transfections of HeLa cells with kChit/DNA polyplexes at different N/P ratios revealed that the highest transfection of a population of cells was observed at N/P ratios of 20 and 50. See FIG. 5. After 24 hours of cell growth post transfection, about 20% of HeLa cells were producing GFP. Transfection was observed at other N/P ratios but at smaller amount (FIG. 6A). In contrast, kChitosan/siRNA silencing is most optimal at higher N/P ratios. For N/P ratios of 100 and 200, an almost 100% reduction in expression is observed (FIG. 6B). At higher N/P ratios of 300 and 400, the silencing efficiency decreases. Though there is a reduction in eGFP expression, some cell death was observed. Consequently, the death of some of the cells might have contributed to the increase silencing for N/P ratios of 300 and 400.

Cytotoxicity of kChitosan on HeLa Cells.

Figure 7A:
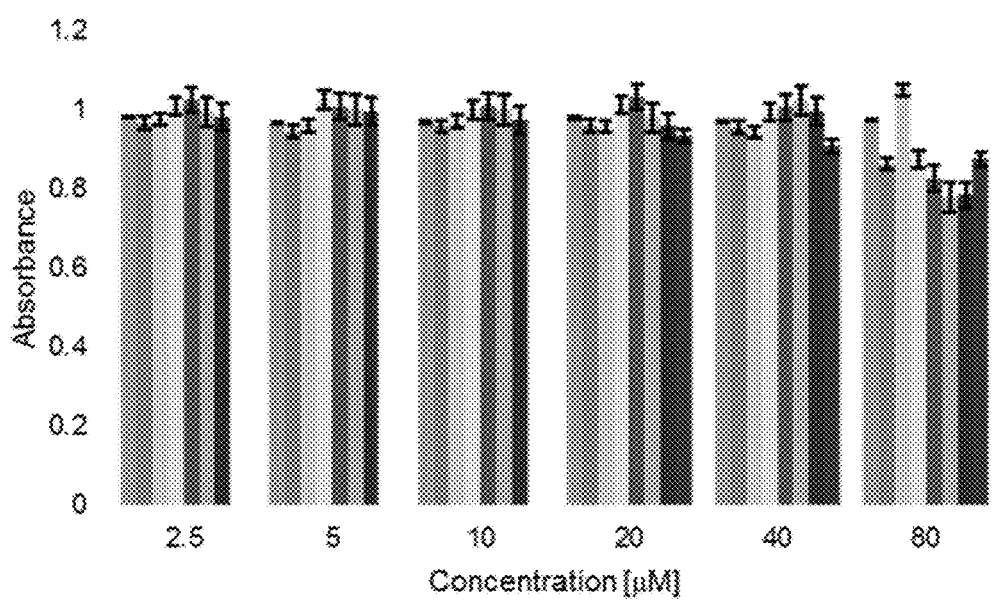
FIGS. 7A-7B. MTT assay histogram of results for indicated compounds in the MTT assay in HeLa cells. Y-axis: absorbance units.
Figure 7B:
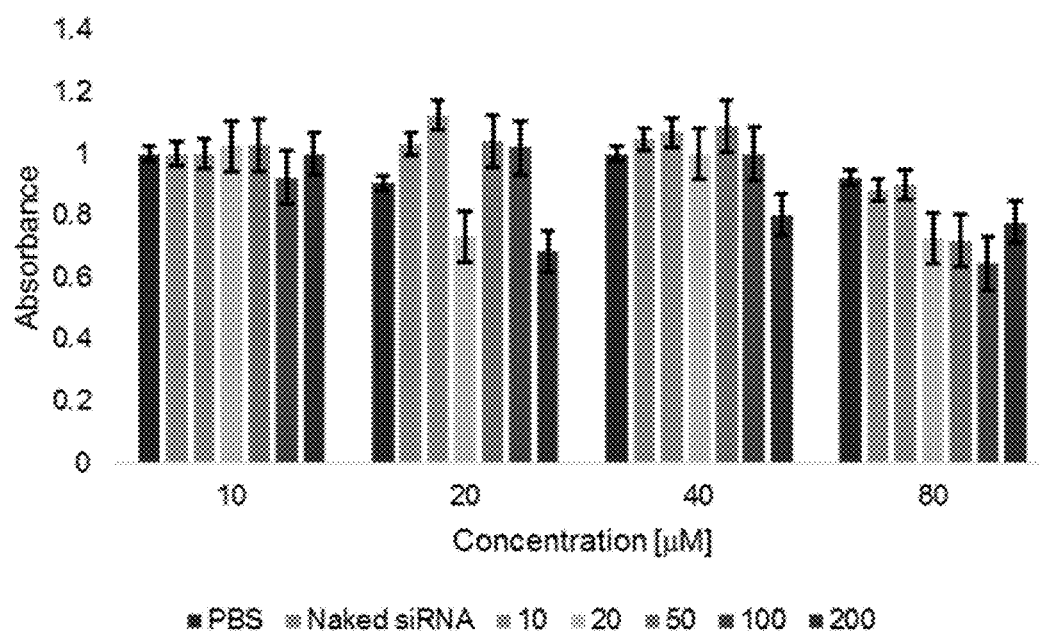

To investigate the potential cytotoxicity of kChitosan/DNA polyplexes, HeLa cell viability was accessed by MTT assay. Over 95% average cell viability was observed for kChitosan/DNA polyplex and naked DNA at 50% diluted concentrations. However, about 20-25% loss of cell viability was observed for polyplexes at 100% concentration. Additionally there was apparent toxicity of about 5% associated with a solution of pure material diluted in PBS. Free DNA did not show toxicity at any concentration, while at the polyplexes at N/P of 50 appeared to be the most cytotoxic (25%) at 100% concentration (FIG. 7A). kChitosan/sirNA showed similarities in toxicity of the polyplex with no drastic toxicity to HeLa cells. See FIG. 7B. At higher concentration of polymer in N/P ratio 200, there were some cell death, but at reduced concentration this is negated. Without wishing to be bound by any theory, the appeared toxicity of the polyplex might be attributed to the release of acetone from the ketal linkage upon hydrolysis, or might also be an effect of the membrane permeability properties of chitosan.

Exemplary embodiments include the following.

Embodiment 1p

A ketal-chitosan, having structure

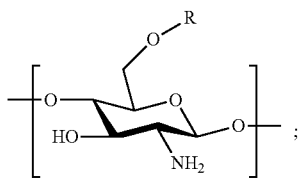

wherein R is an optionally substituted heteroalkyl moiety forming a ketal with the chitosan monomer.

Embodiment 2p

A method for synthesis of a ketal chitosan, the method including protecting a chitosan monomer, reacting the protected chitosan with a half acetal moiety under conditions suitable to form a protected ketal chitosan, and deprotecting the protected ketal chitosan, thereby affording a ketal chitosan.

Embodiment 1

A polymeric compound of Formula (I):

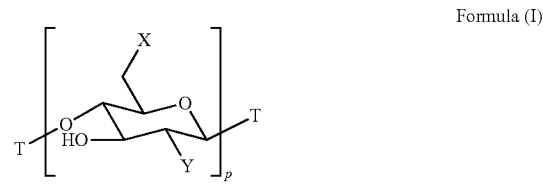

wherein: each Y is independently —$NH_2$, —NH—C(=O)$CH_3$, or a protecting group; each X is independently —OH, —O—C($R^1R^2$)—O—($CH_2$—$CH_2$—O)$_x$—($CH_2$)$_y$—$R^3$, or —O—C($R^1R^2$)—O-D; provided that at least one X is not —OH; p is 2 or more; x and y are each independently an integer from 1 to 10; each T is independently a terminal moiety; $R^1$ and $R^2$ are each independently H, a substituted $C_{1-6}$ alkyl group, an unsubstituted $C_{1-6}$ alkyl group, a substituted heteroalkyl group, or an unsubstituted heteroalkyl group; $R^3$ is —$NH_2$, —C(=O)—$R^4$, or —$NH_2$—C(=O)—$R^4$; and $R_4$ is D, a $C_{1-6}$ alkyl group, or a $C_{1-6}$ alkyl group substituted with one or more halogen atoms; and D is a drug moiety.

Embodiment 2

The compound of Formula (I) wherein 10% to 100% of the Y in the polymeric compound are $NH_2$, and 0% to 90% of the Y in the polymeric compounds are —NH—C(=O)$CH_3$.

Embodiment 3

The compound of Formula (I) wherein 80% to 100% of the Y in the polymeric compound are $NH_2$, and 0% to 20% of the Y in the polymeric compounds are —NH—C(=O)$CH_3$.

Embodiment 4

The compound of Formula (I) wherein 10% to 100% of the X in the polymeric compound are —O—C($R^1R^2$)—O—($CH_2$—$CH_2$—O)$_x$—($CH_2$)$_y$—$R^3$, and 0% to 90% of the X in the polymeric compound are —OH.

Embodiment 5

The compound of Formula (I) wherein 10% to 100% of the X in the polymeric compound are —O—C($R^1R^2$)—O-D, and 0% to 90% of the X in the polymeric compound are —OH.

Embodiment 6

The compound of Formula (I) wherein 10% to 100% of the Y in the polymer compound are —$NH_2$; and 10% to 100% of the X in the polymeric compound are —O—C($R^1R^2$)—O—($CH_2$—$CH_2$—O)$_x$—($CH_2$)$_y$—$R^3$; wherein x and y are each independently from 1 to 4; $R^3$ is —C(=O)—$R^4$; and $R^4$ is a $C_{1-4}$ alkyl group substituted with one or more fluorine atoms.

Embodiment 7

The compound of Formula (I) wherein 10% to 100% of the Y in the polymer compound are —$NH_2$; and 10% to 100% of the X in the polymeric compound are —O—C($R^1R^2$)—O—($CH_2$—$CH_2$—O)$_x$—($CH_2$)$_y$—$R^3$; wherein $R_1$ and $R_2$ are each hydrogen; x and y are each independently 1 or 2; $R_3$ is —C(=O)—$R^4$; and $R^4$ is —$CF_3$.

Embodiment 8

The compound of Formula (I) wherein 10% to 100% of the Y in the polymer compound are —$NH_2$; and 10% to 100% of the X in the polymeric compound are —O—C($R^1R^2$)—O—($CH_2$—$CH_2$—O)$_x$—($CH_2$)$_y$—$R^3$; wherein x and y are each independently an integer from 1 to 4; $R_3$ is —$NH_2$—C(=O)—$R^4$; and $R^4$ is a $C_{1-4}$ alkyl group substituted with one or more fluorine atoms.

Embodiment 9

The compound of Formula (I) wherein 10% to 100% of the Y in the polymer compound are —$NH_2$; and 10% to 100% of the X in the polymeric compound are —O—C($R^1R^2$)—O—($CH_2$—$CH_2$—O)$_x$—($CH_2$)$_y$—$R^3$; wherein $R_1$ and $R_2$ are each hydrogen; x and y are each independently 1 or 2; $R_3$ is —$NH_2$—C(=O)—$R^4$; and $R^4$ is —$CF_3$.

Embodiment 10

The compound of Formula (I) wherein 10% to 100% of the Y are a protecting group; 10% to 90% of the Y are $NH_2$; and 0% to 90% of the Y are —NH—C(=O)$CH_3$.

Embodiment 11

A pharmaceutical composition comprising the compound of Formula (I) and a pharmaceutically acceptable excipient.

Embodiment 12

A method of treating a bacterial infection in a subject in need thereof comprising administering a therapeutically effective amount of the compound of Formula (I) to the subject to treat the bacterial infection. The subject can be a human.

Embodiment 13

A polymeric compound of Formula (II): A-(L-B)$_p$ wherein A is chitosan; L is a cleavable linking group; B is a drug; a hydrophilic group; or a hydrophilic group linked to a drug; and p is an integer greater than 2.

Embodiment 14

The compound of Formula (II) wherein B is a hydrophilic group.

Embodiment 15

The compound of Formula (II) wherein B is an antibiotic.

Embodiment 16

The compound of Formula (II) wherein L is chemically cleavable or enzymatically cleavable.

Embodiment 17

The compound of Formula (II) wherein L comprises a polyether group, hydroxyl group, a carbonyl group, a carboxyl group, an amino group, a sulfhydryl group, or a phosphate group.

Embodiment 18

A method of treating a bacterial infection in a subject in need thereof comprising administering a therapeutically effective amount of the compound of Formula (II) to the subject to treat the bacterial infection.

What is claimed is:
1. A polymeric compound of Formula (I):

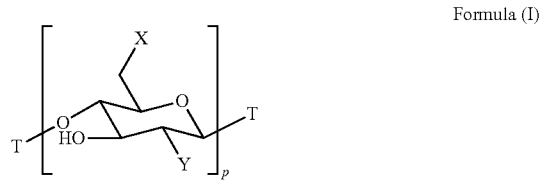

Formula (I)

wherein:
each Y is independently: —$NH_2$ or a protected amine;
each X is independently: —OH, or
—O—C($R^1R^2$)—O—($CH_2$—$CH_2$—O)$_x$—($CH_2$)$_y$—$R^3$,
provided that at least one X is not —OH;
p is 2 or more;
x and y are each independently an integer from 1 to 10;
each T is independently a terminal moiety;
$R^1$ and $R^2$ are each independently H, a substituted $C_{1-6}$ alkyl group, an unsubstituted $C_{1-6}$ alkyl group, a substituted $C_{5-6}$ heteroalkyl group, or an unsubstituted $C_{5-6}$ heteroalkyl group;
$R^3$ is —$NH_2$, —C(=O)—$R^4$, or —$NH_2$—C(=O)—$R^4$; and
$R^4$ is a drug moiety, a $C_{1-6}$ alkyl group, or a $C_{1-6}$ alkyl group substituted with one or more halogen atoms.
2. The compound of claim 1, wherein the protected amine is —NH-C(=O)$CH_3$.
3. The compound of claim 1, wherein
10% to 100% of the X in the polymeric compound are —O—C($R^1R^2$)—O—($CH_2$—$CH_2$—O)$_x$—($CH_2$)$_y$—$R^3$, and
0% to 90% of the X in the polymeric compound are —OH.
4. The compound of claim 1, wherein
$R^1$ and $R^2$ are each independently H or a $C_{1-4}$ alkyl; and
$R^4$ is a $C_{1-4}$ alkyl group or a $C_{1-4}$ alkyl group substituted with one or more halogen atoms.
5. The compound of claim 1, wherein
$R^1$ and $R^2$ are each independently H, —$CH_3$, or —$CH_2CH_3$; and
$R^4$ is —$CH_3$ substituted with one or more halogen atoms or —$CH_2CH_3$ substituted with one or more halogen atom.

6. The compound of claim 1, wherein
10% to 100% of the Y in the polymer compound are —NH$_2$; and
10% to 100% of the X in the polymeric compound are —O—C(R$^1$R$^2$)—O—(CH$_2$—CH$_2$—O)$_x$—(CH$_2$)$_y$—R$^3$;
wherein x and y are each independently from 1 to 4;
R$^3$ is —C(=O)—R$^4$; and
R$^4$ is a C$_{1-4}$ alkyl group substituted with one or more fluorine atoms.

7. The compound of claim 6, wherein
R$_1$ and R$_2$ are each hydrogen;
x and y are each independently 1 or 2; R$_3$ is —C(=O)—R$^4$; and
R$^4$ is —CF$_3$.

8. The compound of claim 1, wherein
10% to 100% of the Y in the polymer compound are —NH$_2$; and
10% to 100% of the X in the polymeric compound are —O—C(R$^1$R$^2$)—O—(CH$_2$—CH$_2$—O)$_x$—(CH$_2$)$_y$—R$^3$;
wherein x and y are each independently an integer from 1 to 4;
R$_3$ is —NH$_2$—C(=O)—R$^4$; and
R$^4$ is a C$_{1-4}$ alkyl group substituted with one or more fluorine atoms.

9. The compound of claim 8, wherein
R$_1$ and R$_2$ are each hydrogen;
x and y are each independently 1 or 2; R$_3$ is —NH$_2$—C(=O)—R$^4$; and
R$^4$ is —CF$_3$.

10. A pharmaceutical composition comprising the compound of claim 1 and a pharmaceutically acceptable excipient.

11. A method of treating a bacterial infection in a subject in need thereof comprising administering a therapeutically effective amount of the compound of claim 1 to the subject to treat the bacterial infection.

12. The compound of claim 1, wherein the drug moiety is an antibiotic.

13. The compound of claim 1, wherein the drug moiety is a tuberculosis drug.

14. The compound of claim 1, wherein the drug moiety is a chemotherapeutic agent.

15. A method of treating a bacterial infection in a subject in need thereof comprising administering a therapeutically effective amount of the compound of claim 12 to the subject to treat the bacterial infection.

16. A method of treating tuberculosis in a subject in need thereof comprising administering a therapeutically effective amount of the compound of claim 13 to the subject to treat the tuberculosis.

17. The compound of claim 1, wherein the protected amine is phthalimide.

18. The compound of claim 2 wherein
80% to 100% of the Y in the polymeric compound are NH$_2$, and
0% to 20% of the Y in the polymeric compounds are —NH-C(=O)CH$_3$.

19. The compound of claim 18, wherein 10 to 100% of the Y are —NH$_2$ and 0 to 90% of the Y are —NH—C(=O)CH$_3$.

20. The compound of claim 1, wherein the protected amine is phthalimide or —NH—C(=O)CH$_3$.

21. The compound of claim 1, wherein the protected amine is selected from the group consisting of —NH—C(=O)CH$_3$, phthalimide, 9-fluorenylmethyl carbamate, t-butyl carbamate, benzyl carbamate, acetamide, trifluoroacetamide, benzylamine, triphenylmethylamine, benzylideneamine and p-toluenesulfonamide.

* * * * *